(12) United States Patent
Fang et al.

(10) Patent No.: US 6,211,392 B1
(45) Date of Patent: Apr. 3, 2001

(54) METHOD OF MANUFACTURING FERROCENYL-1,3-BUTADIENE

(75) Inventors: Jim-Min Fang; Shean-Jeng Jong, both of Taipei (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/520,505

(22) Filed: Mar. 8, 2000

(51) Int. Cl.[7] .............................. C07F 17/02; B01J 27/06
(52) U.S. Cl. .................... 556/143; 502/224; 149/19.2
(58) Field of Search .............................. 556/143; 502/224

(56) References Cited

U.S. PATENT DOCUMENTS 3,739,004 * 6/1973 Ponder et al. ................ 260/429 CY
3,843,426 * 10/1974 Huskins et al. .................... 149/19.2

* cited by examiner

*Primary Examiner*—Porfirio Nazario-Gonzalez
(74) *Attorney, Agent, or Firm*—Jiawei Huang; J C Patents

(57) ABSTRACT

The present invention relates to a method of manufacturing ferrocenyl-1,3-butadiene, in which a ferrocenecarbonyl is reacted with an allyl halide in a polar aprotic solvent lacking a carbonyl group and containing a samarium diiodide in a temperature range.

28 Claims, 1 Drawing Sheet

R=H, $C_6H_5$, $C_1$ - $C_4$ Hydrocarbon

X=Cl, Br, I

R=H, $C_6H_5$, $C_1$ - $C_4$ Hydrocarbon

X=Cl, Br, I

METHOD OF MANUFACTURING FERROCENYL-1,3-BUTADIENE

BACKGROUND OF THE INVENTION

1. Field of Invention

The present invention relates to a method for manufacturing ferrocenyl-1,3-butadiene. More particularly, the present invention relates to a ferrocenyl-1,3-butadiene synthesis method with a relatively high yield and low pollution.

2. Description of Related Art

In U.S. Pat. Nos. 3,739,004 and 3,843,426, it has been found that ferrocenyl-1,3-butadiene is an important starting material for manufacturing copolymer and homopolymer and is employed in applications such as the coating material for aerospace transportation to enhance resistance to photo degradation, ultraviolet rays and gamma rays. Ferrocenyl-1,3-butadiene also can be employed as an enhancement fuel in solid propellant. The fuel of the solid propellant comprises aluminum powder and ammonium perchlorate. Additionally, ferrocenyl-1,3-butadiene not only can be an enhancement fuel in solid propellant but also can decrease binder use. Moreover, ferrocenyl alkenes can be employed in electronic materials.

Several processes to synthesize ferrocenyl-1,3-butadiene have already been proposed. However, the prior techniques possess several disadvantages that decrease the yield and the probability of increasing the throughput. The first method for synthesizing ferrocenyl-1,3-butadiene is the method utilizing Wittg reaction as shown in the following equation (I):

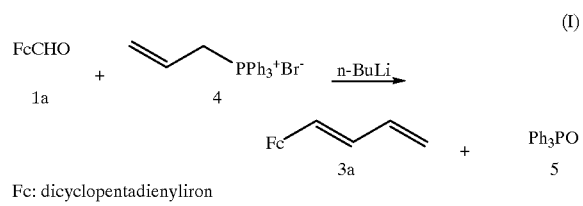

Fc: dicyclopentadienyliron

The disadvantage of the method described above is that the reactant, allyltriphenylphosphonium bromide, is ten times more expensive than allyl bromide and the throughput of the ferrocenyl-1,3-butadiene produced by this method is only 52%. Incidentally, the by-product, $Ph_3PO$ will not be easily removed and remains in the product.

The second method for synthesizing ferrocenyl-1,3-butadiene utilizes allyllithium as reagent and the equation of the method is indicated as equation (II) as shown below:

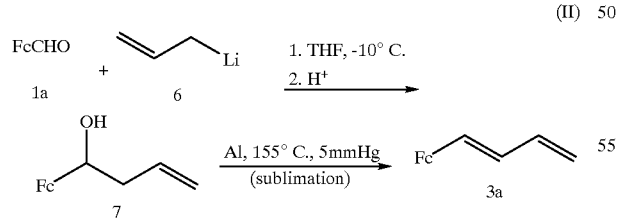

The method described above comprises two steps. First of all, allyllithium is synthesized by allyl bromide. Then, ferrocenyl-1,3-butadiene is formed in dehydration conditions of high temperature and low pressure. This is not a proper way to obtain a high throughput of ferrocenyl-1,3-butadiene.

The third method for synthesizing ferrocenyl-1,3-butadiene utilizes allylmagnesium bromide as a synthesis reagent and the equation of the method is indicated as equation (III) as shown below:

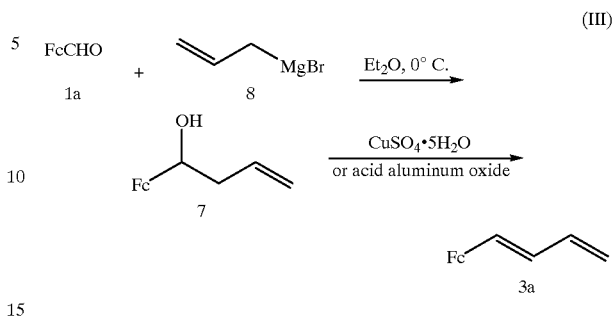

The method described above also comprises two steps. In the dehydration reaction in the second step, if cupric sulfate is used as a dehydration reagent, the dehydrated water should be collected by the Dean-Stark distillatory. However, the throughput of ferrocenyl-1,3-butadiene in this method is just about 50–60% and cannot even be handled. If acidic aluminum oxide is used as a dehydration reagent, the use of aluminum oxide is ten times higher than that of the reagent. Hence, extending the throughput of ferrocenyl-1,3-butadiene by this method is improper.

The fourth method for synthesizing ferrocenyl-1,3-butadiene uses graphite-supported active zinc as a reagent and the equation of the method is indicated as equation (IV) as shown below:

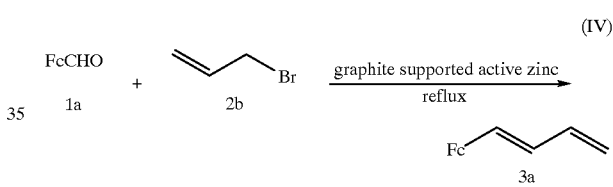

The reagent is not a commercially available product. When preparing the reagent, potassium should be heated to a melting state, and then the melted potassium is powdered and mixed with graphite. After that, the mixture described above is used to reduce the anhydrous zinc chloride into ultra-fine active zinc powder. Usually, the throughput of ferrocenyl-1,3-butadiene reaches 85%. But if the active zinc powder is not fine enough, the yield is decreased. Therefore, it is hard to control the condition for synthesizing ferrocenyl-1,3-butadiene by using this method. Additionally, potassium is a highly active metal. If the operation is improperly or carelessly performed, an explosion is easily induced. Therefore, extending the throughput of ferrocenyl-1,3-butadiene by this method is improper.

SUMMARY OF THE INVENTION

The invention provides a method of manufacturing ferrocenyl-1,3-butadiene, comprising the steps of reacting a ferrocenecarbonyl with an allyl halide in a polar aprotic solvent lacking a carbonyl group and containing a samarium diiodide in a temperature range.

The invention offers a method for manufacturing ferrocenyl-1,3-butadiene with a structure VII (shown below) that uses the reaction of ferrocenecarbonyl with a structure V (shown below) and allyl halides with a structure VI (shown below) with samarium diiodide at 0° C. to room temperature. The reaction is clean, and the product is easily separated from the reaction mixture in very high yields (93–99%). Moreover, the catalytic amounts of samarium diiodide are used for the synthesis of ferrocenyl-1,3-butadienes. Magnesium is used to promote the recycle of samarium diiodide in the reactions.

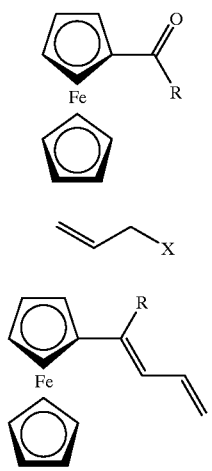

Because of the high reduction ability of samarium diiodide, allyl halides are converted into allylsamarium. Moreover, samarium diiodide can be reacted with ferrocenecarbonyl to reach the addition reaction and the samarium trivalent cation can promote the dehydration of the alcohol intermediate.

Additionally, the synthesis method provided by the invention is a one-pot reaction. Incidentally, the reaction is mild, danger is low, less pollution is produced and the condition of the reaction is easily controlled. Furthermore, the product of the reaction is easily separated and the yield of the reaction is high.

In the invention, the catalytic amounts of samarium diiodide are coordinated with cheap magnesium to produce ferrocenyl-1,3-butadiene. Therefore, the cost of manufacturing ferrocenyl-1,3-butadiene can be decreased.

It is to be understood that both the foregoing general description and the following detailed description are exemplary, and are intended to provide further explanation of the invention as claimed.

BRIEF DESCRIPTION OF THE DRAWINGS

The accompanying drawing is included to provide a further understanding of the invention, and is incorporated in and constitutes a part of this specification. The drawing illustrates embodiments of the invention and, together with the description, serves to explain the principles of the invention.

DESCRIPTION OF THE PREFERRED EMBODIMENTS

Figure 1:
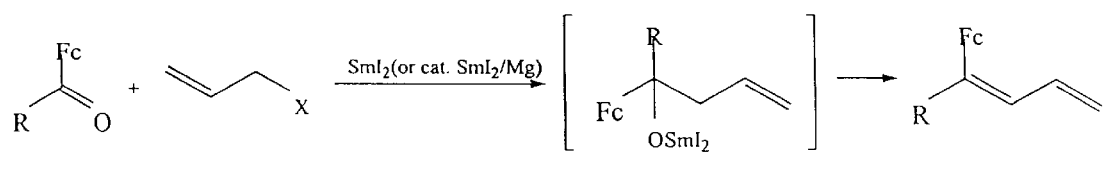
FIG. 1 is the synthesis equation for forming ferrocenyl-1,3-butadiene by using samarium trivalent cation to promote the dehydration of the alcohol intermediate according to this invention.

The invention offers a method for manufacturing ferrocenyl-1,3-butadiene (denoted as VII shown below) by using the reaction of ferrocenecarbonyl (denoted as V shown below) and allyl halides (denoted as VI shown below) with samarium diiodide in a temperature range and in a polar aprotic solvent lacking a carbonyl group. The polar aprotic solvent comprises linear ether solvent, cyclic ether solvent or a combination of both. Preferably, the polar aprotic solvent comprises diethyl ether solvent, tetrahydrofuran solvent or a combination of both. The temperature range is about –20 to 110° C. Preferably, the temperature range is about 0 to 68° C. The reaction is clean and the product is easily separated from the reaction mixture in very high yields (93–99%). Incidentally, a molar ratio of the samarium diiodide to the ferrocenecarbonyl is in a range of about 0.1–100. Preferably, a molar ratio of samarium diiodide to the ferrocenecarbonyl is in a range of about 1–5. Furthermore, a molar ratio of the allyl halide to the ferrocenecarbonyl is in a range of about 1–100. Preferably, a molar ratio of the allyl halide to the ferrocenecarbonyl is in a range of about 1–5. Moreover, a ratio of the polar aprotic solvent lacking a carbonyl group to the ferrocenecarbonyl is about 0.01–100 liters per unit mole. Preferably, a ratio of the polar aprotic solvent lacking a carbonyl group to the ferrocenecarbonyl is about 10–50 liters per unit mole.

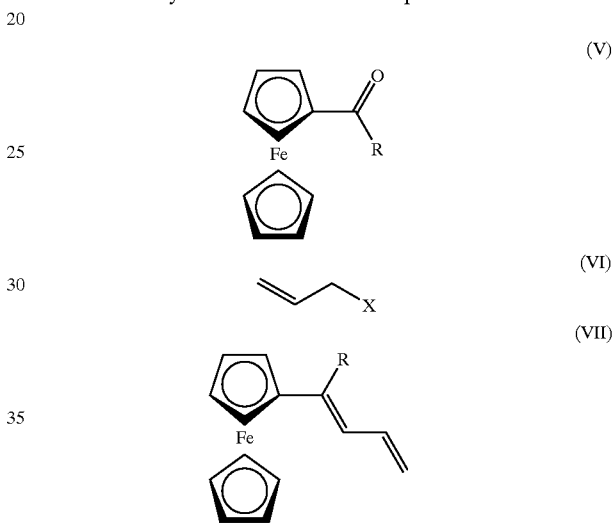

Moreover, catalytic amounts of samarium diiodide can be used for the synthesis of ferrocenyl-1,3-butadienes. Magnesium can be used to promote the recycle of samarium diiodide in the reactions. By using magnesium to improve the recycling of samarium diiodide, a molar ratio of the samarium diiodide to ferrocenecarbonyl is in a range of about 0.01–10. Preferably, a molar ratio of samarium diiodide to the ferrocenecarbonyl is in a range of about 0.1–5. Moreover, a ratio of the magnesium to the ferrocenecarbonyl is in a range of about 1–100. Preferably, a ratio of the magnesium to the ferrocenecarbonyl is in a range of about 1–5.

Because of the high reduction ability of samarium diiodide, allyl halides are converted into allylsamarium. Moreover, the addition reaction of samarium diiodide and ferrocenecarbonyl is performed and the samarium trivalent cation can promote the dehydration of the alcohol intermediate (as shown in FIG. 1). In FIG. 1, a substituent group R of the ferrocenecarbonyl comprises hydrogen, benzyl group or hydrocarbon group comprising one to four carbons. Additionally, the allyl halide comprises allyl chloride, allyl bromide or allyl iodide.

The following examples, given solely by way of indication, illustrate the invention more clearly.

EXAMPLE 1

Synthesis of ferrocenyl-1,3-butadiene (3a) is represented by the following equation (VIII):

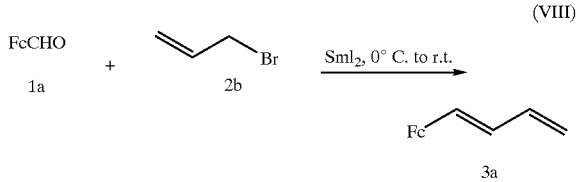

(VIII)

In a nitrogen environment, about 330 mg (2.20 mmole) of samarium and about 500 mg (1.77 mmole) of 1,2-diiodoethane are disposed in a round-bottomed flask. About 20 ml of tetrahydrofuran is added into the round-bottomed flask. The mixture in the round-bottomed flask is stirred for 30 min until a deep-blue samarium diiodide solution is attained. About 242 mg (2.0 mmole) of allyl bromide is dissolved in about 5 ml of tetrahydrofuran. The tetrahydrofuran solution containing allyl bromide is instilled into the samarium diiodide solution. About 257 mg (1.20 mmole) of ferrocenecarbaldehyde is dissolved in about 5 ml of tetrahydrofuran. The tetrahydrofuran solution containing ferrocenecarbaldehyde is instilled into the samarium diiodide solution. The samarium diiodide solution containing allylbromide and ferrocenecarbaldehyde is stirred for about 10 min. Then the samarium diiodide solution containing allylbromide and ferrocenecarbaldehyde is stirred, uncovered, at room temperature for about 15 hr without capping. The reaction mixture is introduced into a short silica gel column. A column separation process is performed and a solvent comprising ethyl acetate and n-hexane (1:1) is used as an eluent. After drying and evaporation of the eluent solvent, the residual solid product is ferrocenyl-1,3-butadiene (3a) with a weight of about 280 mg (1.18 mmole) and a yield of about 98%.

The melting point of the solid product, ferrocenyl-1,3-butadiene (3a), is about 87–88° C. Additionally, in $^1$H NMR (nuclear magnetic resonance) spectrum (300 MHz, CDCl$_3$), the main peaks of ferrocenyl-1,3-butadiene (3a) comprise δ4.11 (5H, s, Fc), 4.23 (2H, s, Fc), 4.34 (2H, s, Fc), 5.01–5.05 (1H, m, H-4), 5.14–5.20 (1H, m, H-4) and 6.32–6.43 (3H, m, H-1, 2, 3). Moreover, the calculated weight of C$_{14}$H$_{14}$Fe the formula of ferrocenyl-1,3-butadiene (3a) is about 238.0445 and a peak about [M]$^+$m/z 238.0437 is found in High Resolution Fast Atom Bombardment Mass Spectrometry (HR-FABMS).

EXAMPLE 2

Synthesis of 1-Ferrocenyl-1-methyl-1,3-butadiene (3b) is represented by the following equation (IX):

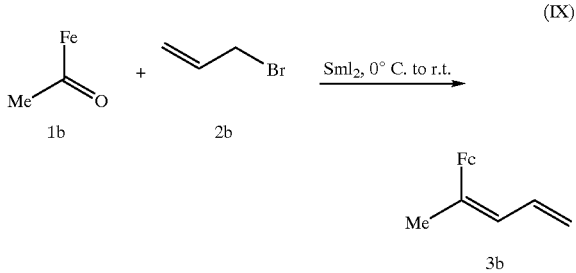

(IX)

According to the step flow described in Example 1, about 274 mg (1.20 mmole) of ferrocenyl methyl ketone react with 242 mg (2.0 mmole) of allyl bromide and 1.77 mmole of samarium diiodide in a temperature range of about 0° C. to room temperature to produce an oil-type 1-Ferrocenyl-1-methyl-1,3-butadiene (3b) with a weight of about 302 mg (1.19 mmole) and a yield of about 99%.

Additionally, in $^1$H NMR (nuclear magnetic resonance) spectrum (300 MHz, CDCl$_3$), the main peaks of 1-Ferrocenyl-1-methyl-1,3-butadiene (3b) comprise δ2.11 (3H, s, CH$_3$), 4.10 (5H, s, Fc), 4.23 (2H, s, Fc), 4.40 (2H, s, Fc), 5.07 (1H, d, J=10.0 Hz, H-4), 5.22 (1H, d, J=16.7 Hz, H-4), 6.30 (1H, d, J=11.0 Hz, H-2) and 6.67 (1H, ddd, J=10.0, 11.0, 16.7 Hz, H-3). Moreover, the calculated element-weight ratio of C$_{15}$H$_{16}$Fe, the formula of 1-Ferrocenyl-1methyl-1,3-butadiene (3b), is about C: 71.45% and H: 6.40%, while an experimental value of about C: 71.57% and H: 6.71% is found in elemental analysis.

EXAMPLE 3

Synthesis of 1-Ferrocenyl-1-methyl-1,3-butadiene (3b) is represented by the following equation (X):

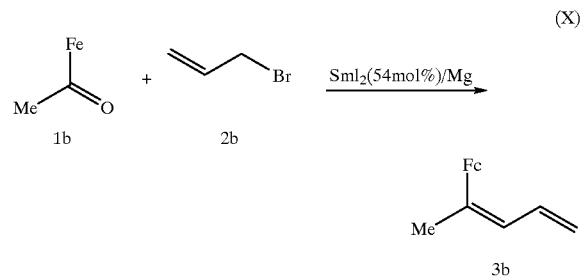

(X)

In a nitrogen environment, about 0.72 mg (3.0 mmole) of magnesium and about 6 ml of deep-blue tetrahydrofuran solution containing about 0.54 mmole of samarium diiodide are disposed in a 50 ml round-bottomed flask. About 228 mg (1.0 mmole) of acetylferrocene and about 181.5 mg (1.5 mmole) of allyl bromide are together dissolved in 20 ml of tetrahydrofuran. The tetrahydrofuran solution containing acetylferrocene and allylbromide is introduced into the 50 ml round-bottomed flask containing magnesium and samarium diiodide in tetrahydrofuran solution. The mixture in the uncovered 50 ml round-bottomed flask is stirred for 30 min. The capping serum septum is removed and the mixture is stirred at room temperature for 2 hr. After that, reflux of the solution is performed for about 2 hr. The reacted solution is introduced into a short silica gel column. A column separation process is performed and a solvent comprising ethyl acetate and n-hexane (1:1) is used as an eluent. After drying and evaporation of the eluent solvent, the oil-type residual product is 1-Ferrocenyl-1-methyl-1,3-butadiene (3b) with a weight of about 250 mg (0.99 mmole) and a yield of about 99%.

EXAMPLE 4

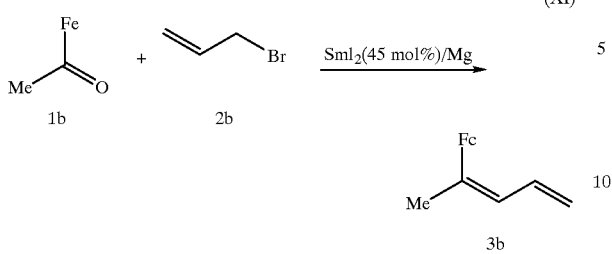

Synthesis of 1-Ferrocenyl-1-methyl-1,3-butadiene (3b) is represented by the following equation (XI):

In a nitrogen environment, about 0.72 mg (3.0 mmole) of magnesium and about 5 ml of deep-blue tetrahydrofuran solution containing about 0.45 mmole of samarium diiodide are disposed in a 50 ml round-bottomed flask. About 228 mg (1.0 mmole) of acetylferrocene and 221 mg (1.0 mmole) of allyl bromide are together dissolved in 30 ml of diethyl ether. The diethyl ether solution containing acetylferrocene and allylbromide is introduced into the 50 ml round-bottomed flask containing magnesium and samarium diiodide in tetrahydrofuran solution. The mixture in the 50 ml round-bottomed flask is stirred for 30 min. The capping serum septum is removed and the mixture is stirred at room temperature for 24 hr. After that, reflux of the solution is performed for about 24 hr. The reacted solution is introduced into a short silica gel column. A column separation process is performed and a solvent comprising ethyl acetate and n-hexane (1:1) is used as an eluent. After drying and evaporation of the eluent solvent, the oil-type residual product is 1-Ferrocenyl-1-methyl-1,3-butadiene (3b) with a weight of about 246 mg (0.93 mmole) and a yield of about 93%.

EXAMPLE 5

Synthesis of 1-Ferrocenyl-1-methyl-1,3-butadiene (3b) by using catalytic amounts of samarium diiodide is represented by the following equation (XII):

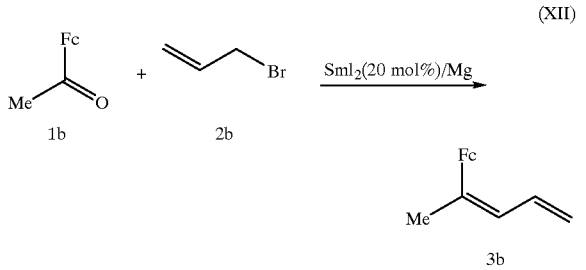

In a nitrogen environment, about 0.72 mg (3.0 mmole) of magnesium and about 2 ml of deep-blue tetrahydrofuran solution containing about 0.20 mmole of samarium diiodide are disposed in a 50 ml round-bottomed flask. About 228 mg (1.0 mmole) of acetylferrocene and 181.5 mg (1.5 mmole) of allyl bromide are together dissolved in 20 ml of tetrahydrofuran. The tetrahydrofuran solution containing acetylferrocene and allyl bromide is introduced into the 50 ml round-bottomed flask containing magnesium and samarium diiodide in tetrahydrofuran solution. The mixture in the uncovered 50 ml round-bottomed flask is stirred for 30 min. The capping serum septum is removed and the mixture is stirred at room temperature for 2 hr. After that, reflux of the solution is performed for about 72 hr. The reacted solution is introduced into a short silicon gel column. A column separation process is performed and a solvent comprising ethyl acetate and n-hexane (1:1) is used as an eluent. After drying and evaporation of the eluent solvent, the oil-type residual product is 1-Ferrocenyl-1-methyl-1,3-butadiene (3b) with a weight of about 252 mg (1.0 mmole) and a yield of about 100%.

EXAMPLE 6

Synthesis of 1-Ferrocenyl-1-phenyl-1,3-butadiene (3c) is represented by the following equation (XIII):

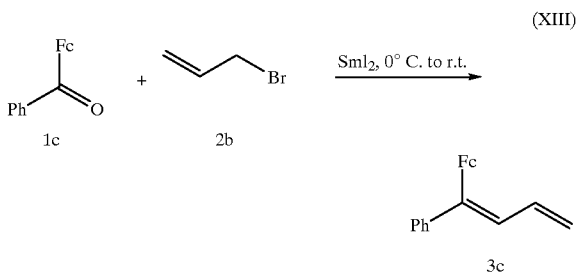

In a nitrogen environment, about 330 mg (2.20 mmole) of samarium and about 500 mg (1.77 mmole) of 1,2-diiodoethane is disposed in a round-bottomed flask. About 20 ml of tetrahydrofuran is added into the round-bottomed flask. The mixture in the round-bottomed flask is stirred until a deep-blue samarium diiodide solution is obtained. Following the process flow described in Example 1, about 348 mg (1.20 mmole) of benzoylferrocene reacts with about 242 mg (2.0 mmole) of allyl bromide to produce oil-type 1-Ferrocenyl-1-phenyl-1,3-butadiene (3c) with a weight of about 373 mg (1.19 mmole) and a yield of about 99%.

Additionally, in $^1$H NMR (nuclear magnetic resonance) spectrometry (300 MHz, CDCl$_3$), the main peaks of 1-Ferrocenyl-1-phenyl-1,3-butadiene (3c) comprise δ4.14 (5H, s, Fc), 4.23 (4H, m, Fc), 5.02 (1H, d, J=9.7 Hz, H-4), 5.29 (1H, d, J=17.2 Hz, H-4), 6.25 (1H, ddd, J=9.7, 11.1, 17.2 Hz, H-3), 6.63 (1H, J=11.1 Hz, H-2) and 7.31–7.46 (5H, m, Ph). Moreover, the calculated weight of C$_{20}$H$_{18}$Fe, the formula of 1-Ferrocenyl-1-benzyl-1,3-butadiene (3c), is about 314.0758 and a peak about [M]$^+$ m/z 314.0745 is found in HR-FABMS.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method of manufacturing ferrocenyl-1,3-butadiene, comprising:
   reacting a ferrocenecarbonyl with an allyl halide in a polar aprotic solvent lacking a carbonyl group and using a samarium diiodide as a catalyst.

2. The method of claim 1, wherein a substituent group of the ferrocenecarbonyl is selected from a group consisting of hydrogen, phenyl group and hydrocarbon group comprising one to four carbons.

3. The method of claim 1, wherein a molar ratio of the samarium diiodide to the ferrocenecarbonyl is in a range of about 0.1–100.

4. The method of claim 1, wherein a molar ratio of the samarium diiodide to the ferrocenecarbonyl is in a range of about 1–5.

5. The method of claim 1, wherein the allyl halide is selected from a group consisting of chloride, bromide and iodide.

6. The method of claim 1, wherein a molar ratio of the allyl halide to the ferrocenecarbonyl is in a range of about 1–100.

7. The method of claim 1, wherein a molar ratio of the allyl halide to the ferrocenecarbonyl is in a range of about 1–5.

8. The method of claim 1, wherein the polar aprotic solvent lacking a carbonyl group is selected from a group consisting of linear ether solvent, cyclic ether solvent and a combination of both.

9. The method of claim 1, wherein the polar aprotic solvent lacking a carbonyl group is selected from a group consisting of diethyl ether solvent, tetrahydrofuran solvent and a combination of both.

10. The method of claim 1, wherein a ratio of the polar aprotic solvent lacking a carbonyl group to the ferrocenecarbonyl is about 0.01–100 liters per unit mole.

11. The method of claim 1, wherein a ratio of the polar aprotic solvent lacking a carbonyl group to the ferrocenecarbonyl is about 10–50 liters per unit mole.

12. The method of claim 1, wherein the reaction between the ferrocenecarbonyl and the allyl halide is conducted at a temperature in the range of about −20 to 110° C.

13. The method of claim 1, wherein the reaction between the ferrocenecarbonyl and the allyl halide is conducted at a temperature in the range of about 0 to 68° C.

14. A method of manufacturing ferrocenyl-1,3-butadiene, comprising:

reacting a ferrocenecarbonyl with an allyl halide in a polar aprotic solvent lacking a carbonyl group and using a samarium diiodide as a catalyst and a magnesium as a promoter.

15. The method of claim 14, wherein a substituent group of the ferrocenecarbonyl is selected from a group consisting of hydrogen, a phenyl group and a hydrocarbon group comprising one to four carbons.

16. The method of claim 14, wherein a molar ratio of the samarium diiodide to the ferrocenecarbonyl is in a range of about 0.01–10.

17. The method of claim 14, wherein a molar ratio of the samarium diiodide to the ferrocenecarbonyl is in a range of about 0.1–5.

18. The method of claim 14, wherein the allyl halide is selected from a group consisting of chloride, bromide and iodide.

19. The method of claim 14, wherein a molar ratio of the allyl halide to the ferrocenecarbonyl is in a range of about 1–100.

20. The method of claim 14, wherein a molar ratio of the allyl halide to the ferrocenecarbonyl is in a range of about 1–5.

21. The method of claim 14, wherein the polar aprotic solvent lacking a carbonyl group is selected from a group consisting of linear ether solvent, cyclic ether solvent and a combination of both.

22. The method of claim 14, wherein the polar aprotic solvent lacking a carbonyl group is selected from a group consisting of diethyl ether solvent, tetrahydrofuran solvent and a combination of both.

23. The method of claim 14, wherein a ratio of the polar aprotic solvent lacking a carbonyl group to the ferrocenecarbonyl is about 0.01–100 liters per unit mole.

24. The method of claim 14, wherein a ratio of the polar aprotic solvent lacking a carbonyl group to the ferrocenecarbonyl is about 10–50 liters per unit mole.

25. The method of claim 14, wherein the reaction between the ferrocenecarbonyl and the allyl halide is conducted at a temperature in the range of about −20 to 110° C.

26. The method of claim 14, wherein the reaction between the ferrocenecarbonyl and the allyl halide is conducted at a temperature in the range of about 0 to 68° C.

27. The method of claim 14, wherein a ratio of the magnesium to the ferrocenecarbonyl is in a range of about 1–100.

28. The method of claim 14, wherein a ratio of the magnesium to the ferrocenecarbonyl is in a range of about 1–5.

* * * * *